US010501507B2

(12) United States Patent
O'Keefe et al.

(10) Patent No.: US 10,501,507 B2
(45) Date of Patent: Dec. 10, 2019

(54) GRIFFITHSIN MUTANTS

(71) Applicants: The United States of America, as represented by the Secretary, Department of Health and Human Services, Bethesda, MD (US); University of Louisville Research Foundation, Inc., Louisville, KY (US); University of Pittsburgh-Of the Commonwealth System of Higher Education, Pittsburgh, PA (US)

(72) Inventors: Barry R. O'Keefe, Frederick, MD (US); Tinoush Moulaei, College Park, MD (US); Kenneth E. Palmer, Owensboro, KY (US); Lisa C. Rohan, Pittsburgh, PA (US); Joshua L. Fuqua, Owensboro, KY (US); Lindsay F. Kramzer, Pittsburgh, PA (US)

(73) Assignees: The United States of America, as represented by the Secretary, Department of Health and Human Services, Bethesda, MD (US); University of Louisville Research Foundation, Inc., Louisville, KY (US); University of Pittsburgh—Of the Commonwealth System of Higher Education, Pittsburgh, PA (US)

( * ) Notice: Subject to any disclaimer, the term of this patent is extended or adjusted under 35 U.S.C. 154(b) by 0 days.

(21) Appl. No.: 15/550,323

(22) PCT Filed: Feb. 10, 2016

(86) PCT No.: PCT/US2016/017267
§ 371 (c)(1),
(2) Date: Aug. 10, 2017

(87) PCT Pub. No.: WO2016/130628
PCT Pub. Date: Aug. 18, 2016

(65) Prior Publication Data
US 2018/0016307 A1 Jan. 18, 2018

Related U.S. Application Data

(60) Provisional application No. 62/114,217, filed on Feb. 10, 2015.

(51) Int. Cl.
*A61K 38/16* (2006.01)
*C07K 14/405* (2006.01)
*A61K 38/00* (2006.01)

(52) U.S. Cl.
CPC ............ *C07K 14/405* (2013.01); *A61K 38/16* (2013.01); *A61K 38/00* (2013.01)

(58) Field of Classification Search
None
See application file for complete search history.

(56) References Cited

U.S. PATENT DOCUMENTS

| | | | |
|---|---|---|---|
| 5,424,398 | A | 6/1995 | Middeldorp et al. |
| 5,843,882 | A | 12/1998 | Boyd et al. |
| 7,494,798 | B2 | 2/2009 | Berka et al. |
| 7,884,178 | B2 | 2/2011 | Boyd et al. |
| 8,008,729 | B2 | 8/2011 | Graf et al. |
| 8,067,530 | B2 | 11/2011 | O'Keefe et al. |
| 8,088,729 | B2 | 1/2012 | O'Keefe et al. |
| 8,394,764 | B2 | 3/2013 | Boyd et al. |
| 2014/0274883 | A1 | 9/2014 | Van Olphen et al. |

FOREIGN PATENT DOCUMENTS

| | | | |
|---|---|---|---|
| WO | WO 2005/118627 | A2 | 12/2005 |
| WO | WO 2014/197650 | A1 | 12/2014 |

OTHER PUBLICATIONS

Banerjee et al, "Occluding the mannose moieties on human immunodeficiency virtype 1 gp 120 with griffithsin improves the antibody responses to both proteins in mice," *AIDS Res. Hum. Retrovir.*, 28(2): 206-214 (2012).
Barany et al., "Solid-phase peptide synthesis: a silver anniversary report," *Int. J. Peptide Protein Res.*, 30(6): 705-739 (1987).
Boyd et al., "Anti-HIV michellamines from Ancistrocladkorupensis," *J. Med. Chem.*, 37(12): 1740-1745 (1994).
Brink et al., "Developing efficient strategies for the generation of transgenic cattle which produce biopharmaceuticals in milk" *Theriogenology*, 53(1): 139-148 (2000).
Conrad et al., "Compartment-specific accumulation of recombinant immunoglobulins in plant cells: an essential tool for antibody production and immunomodulation of physiological functions and pathogen activity," *Plant Molec. Biol.*, 38(1-2): 101-109 (1998).
De Wilde et al., "Plants as bioreactors for protein production: avoiding the problem of transgene silencing," *Plant Mol. Biol.*, 43(2-3): 347-359 (2000).
Ferir et al., "Combinations of griffithsin with other carbohydrate-binding agents demonstrate superior activity against HIV Type 1, HIV Type 2, and selected carbohydrate-binding agent-resistant HIV Type 1 strains," *AIDS Res. Hum. Retrovir.*, 28(11): 1513-1523 (2012).
Ferir et al., "Synergistic activity profile of griffithsin in combination with tenofovir, maraviroc and enfuvirtide against HIV-1 clade C," *Virology*, 417(2): 253-258 (2011).
Fischer et al., "Antibody production by molecular farming in plants," *J. Biol. Regul. Homeost. Agents*, 14: 83-92 (2000).
Fischer et al., "Molecular farming of pharmaceutical proteins," *Transgenic Res.*, 9(4-5): 279-299 (2000).
GENBANK Accession No. CAJ75663 (dated Jul. 17, 2006).

(Continued)

*Primary Examiner* — Richard G Hutson
(74) *Attorney, Agent, or Firm* — Leydig, Voit & Mayer, Ltd.

(57) ABSTRACT

The invention provides modified griffithsin polypeptides comprising the amino acid sequence of SEQ ID NO: 1, as well as corresponding nucleic acids, vectors, cells, fusion proteins, constructs, conjugates, and methods of inhibiting viral infection.

16 Claims, No Drawings

Specification includes a Sequence Listing.

(56) References Cited

OTHER PUBLICATIONS

Gulakowski et al., "A semiautomated multiparameter approach for anti-HIV drug screening," *J. Virol. Methods*, 33(1-2): 87-100 (1991).
Houdebine, "Transgenic animal bioreactors," *Transgenic Res.*, 9(4-5): 305-320 (2000).
International Preliminary Report on Patentability, Application No. PCT/US2016/017267, dated Aug. 15, 2017.
International Search Report, Application No. PCT/US2016/017267, dated May 6, 2016.
Ishag et al, "Griffithsin inhibits Japanese encephalitis virinfection in vitro and in vivo," *Arch. Virol.*, 158(2): 349-358 (2013).
Kashman et al., "The calanolides, a novel HIV-inhibitory class of coumarin derivatives from the tropical rainforest tree, *Calophyllum lanigerum*," *J. Med. Chem.*, 35(15): 2735-2743 (1992).
McCormick et al., "Rapid production of specific vaccines for lymphoma by expression of the tumor-derived single-chain Fv epitopes in tobacco plants," *Proc. Natl. Acad. Sci. USA*, 96(2): 703-708 (1999).
Merigan, "Treatment of AIDS with combinations of antiretroviral agents," *Am. J. Med.*, 90(4A): 8S-17S (1991).
Merrifield, "Solid Phase Peptide Synthesis. I. The Synthesis of a Tetrapeptide," *J. Am. Chem. Soc.*, 85: 2149-2154 (1963).
Mori et al., "Isolation and characterization of griffithsin, a novel HIV-inactivating protein, from the red alga *Griffithsia* sp," *J. Biol. Chem.*, 280(10): 9345-9353 (2005).
Moulaei et al, "Monomerization of viral entry inhibitor griffithsin elucidates the relationship between multivalent binding to carbohydrates and anti-HIV activity," *Structure*, 18(9): 1104-1115 (2010).
Moulaei et al., "Griffithsin tandemers: flexible and potent lectin inhibitors of the human immunodeficiency virus," *Retrovirology*, 12(1): 6 (2015).
Nixon et al., "Griffithsin protects mice from genital herpes by preventing cell-to-cell spread," *J. Virol.*, 87(11): 6257-6269 (2013).
O'Keefe et al., "Broad-spectrum in vitro activity and in vivo efficacy of the antiviral protein griffithsin against emerging viruses of the family *Coronaviridae*," *J. Virol.*, 84(5): 2511-2521 (2010).
O'Keefe et al., "Scaleable manufacture of HIV-1 entry inhibitor griffithsin and validation of its safety and efficacy as a topical microbicide component," *Proc. Natl. Acad. Sci. USA*, 106(15): 6099-6104 (2009).
Pollock et al., "Transgenic milk as a method for the production of recombinant antibodies," *J. Immunol. Methods*, 231(1-2): 147-157 (1999).
Shih et al., "Chimeric human immunodeficiency virtype 1/type 2 reverse transcriptases display reversed sensitivity to nonnucleoside analog inhibitors," *Proc. Natl. Acad. Sci. USA*, 88(21): 9878-9882 (1991).
Staub et al., "High-yield production of a human therapeutic protein in tobacco chloropasts," *Nat. Biotechnol.*, 18(3): 333-338 (2000).
Tacket et al., "A review of oral vaccination with transgenic vegetables," *Microbes Infect.*, 1(10): 777-783 (1999).
Tacket et al., "Immunogenicity in humans of a recombinant bacterial antigen delivered in a transgenic potato," *Nature Med.*, 4(5): 607-609 (1998).
Theiss et al., "Iontophoresis—is there a future for clinical application?" *Meth. Find. Exp. Clin. Pharmacol.*, 13(5): 353-359 (1991).
Wallace et al., "Stand and deliver: getting peptide drugs into the body," *Science*, 260(5110): 912-913 (1993).
White et al., "A TIBO derivative, R82913, is a potent inhibitor of HIV-1 reverse transcriptase with heteropolymer templates," *Antiviral Res.*, 16(3): 257-266 (1991).
Written Opinion of the International Searching Authority, Application No. PCT/US2016/017267, dated Aug. 18, 2016.
Xue et al., "The role of individual carbohydrate-binding sites in the function of the potent anti-HIV lectin griffithsin," *Mol. Pharm.*, 9(9): 2613-2625 (2012) Author Manuscript.
Zeitlin et al., "A humanized monoclonal antibody produced in transgenic plants for immunoprotection of the vagina against genital herpes," *Nat. Biotechnol.*, 16(13): 1361-1364 (1998).
Ziolkowska et al., "Domain-swapped structure of the potent antiviral protein griffithsin and its mode of carbohydrate binding," *Structure*, 14(7): 1127-1135 (2006).

GRIFFITHSIN MUTANTS

CROSS-REFERENCE TO RELATED APPLICATIONS

This patent application a U.S. National Phase of International Patent Application No. PCT/US2016/017267, filed Feb. 10, 2016, which claims the benefit of U.S. Provisional Patent Application No. 62/114,217, filed Feb. 10, 2015, which is incorporated by reference.

SEQUENCE LISTING

Incorporated by reference in its entirety herein is a nucleotide/amino acid sequence listing submitted concurrently herewith identified as follows: One 21,639 Byte ASCII (Text) file named "730368_ST25.txt," dated Aug. 9, 2017.

BACKGROUND OF THE INVENTION

Griffithsin is a potent anti-viral protein with activity against HIV and other viruses (see, e.g., U.S. Pat. Nos. 7,884,178, 8,008,729, and 8,394,764; Mori et al., *J. Biol. Chem.*, 280: 9345-9353 (2005); Ziolkowska et al., *Structure*, 14: 1127-35 (2006); O'Keefe et al., *Proc. Natl. Acad. Sci.* (USA), 106: 6099-104 (2009); O'Keefe et al., *J. Virol.* 84: 2511-21 (2010); and Moulaei et al., *Structure*, 18: 1104-15 (2010)).

The need remains for additional griffithsin compounds with improved properties.

BRIEF SUMMARY OF THE INVENTION

The invention provides a polypeptide comprising the amino acid sequence of SLTHRKFGGSGGSPFSGLSSIAVRSGSYLDAIIIDGVHHGGSGGNLSPTFTFGSGEYISN$X_1$TIRSGDYIDNISF$X_2$TN$X_3$GRRFGPYGGSGGSANTLSNVKVIQINGX$_4$X$_5$GDYLDSLD X$_6$YYX$_7$QY (SEQ ID NO: 1), wherein $X_1$ can be M or V, $X_2$ can be E or Q, $X_3$ can be M, A, K, V, F, L, I, Q, R, or G, $X_4$ can be S or R, $X_5$ can be A or S, $X_6$ can be I or F, and $X_7$ can be E or Q provided that SEQ ID NO: 1 does not comprise the amino acid sequence of SEQ ID NO: 2, as well as a conjugate comprising the polypeptide. Nucleic acid molecules encoding the polypeptides and conjugates, vectors comprising the nucleic acid molecules, cells comprising the nucleic acid molecules or vectors, as well as compositions comprising the polypeptides, conjugates, nucleic acid molecules, vectors, and cells also are provided.

The invention also provides a method of inhibiting a viral (e.g., HIV) infection in a cell, host, biological sample, or inanimate object comprising administering the polypeptides, conjugates, nucleic acid molecules, vectors, cells, or compositions, such that the viral infection is inhibited.

DETAILED DESCRIPTION OF THE INVENTION

The invention provides modified griffithsin polypeptides with improved properties, such as reduced methionine oxidation, increased shelf-life, improved solubility, and improved bioavailability at different pH ranges.

The modified griffithsin polypeptides can have a mutation at position 78 (e.g., a Met-Ala mutation) relative to the wild-type griffithsin sequence (SEQ ID NO: 2) which eliminates the possibility of methionine oxidation at this solvent-exposed position. This prevents protein oxidation and increases the usable shelf-life of griffithsin formulations. The modified griffithsin polypeptides can contain an amino acid at position 78 relative to the wild-type griffithsin sequence (SEQ ID NO: 2) that is not charged and contains no sulfur. Exemplary amino acids include Ala, Lys, Val, Gly, Leu, Ile, and Phe. In one embodiment, the griffithsin mutant polypeptide comprises, consists essentially of, or consists of the amino acid sequence of SEQ ID NO: 15. In other embodiments, the griffithsin mutant polypeptide comprises, consists essentially of, or consists of the amino acid sequence of SEQ ID NO: 16 or 17.

Alternatively, the modified griffithsin polypeptides can contain an amino acid at position 78 relative to the wild-type griffithsin sequence (SEQ ID NO: 2) that is charged, such as a basic amino acid (e.g., Glu), which would eliminate Met oxidation and change the pI of the modified griffithsin polypeptides making them more soluble at acidic pH. In one embodiment, the griffithsin mutant polypeptide comprises, consists essentially of, or consists of the amino acid sequence of SEQ ID NO: 18.

The modified griffithsin polypeptides also can contain mutations that change the isoelectric point of the protein (e.g., at positions 75, 78, and 119) and alter its solubility in various pH ranges (e.g., at positions 106 and 107) allowing for improved product release. Additionally, the modified griffithsin polypeptides can contain mutations at positions 61 and 116, which are related to methionine oxidation.

Although not wishing to be bound by any particular theory, altering the isoelectric point (i.e., the pH at which a particular molecule carries no net electrical charge) of the modified griffithsin polypeptides can optimize the bioavailability of the modified griffithsin polypeptides in different compartments of the body (e.g., nasal cavity, lung, gut, small intestine, colon, blood, vagina, and rectum). The pH of wild-type griffithsin of SEQ ID NO: 2 is 5.1. However, the pH of the nasal cavity is about 5.5-6.5, the pH of lung is about 7.3 to 7.5, the pH of the gut is about 1 to 3, the pH of the small intestine is about 5.5 to 7.5, the pH of the colon is about 5.5 to 7, the pH of blood is about 7.3 to 7.5, the pH of vaginal fluid is about 3.8 to 4.5, and the pH of rectal fluid is about 7 to 8. By manipulating the pI of griffithsin through mutation, its pI can be moved away from the pH of the various compartments and thereby increase bioavailability of griffithsin in those compartments.

In particular, the invention provides griffithsin mutant polypeptides comprising, consisting essentially of, or consisting of the amino acid sequence of SLTHRKFGGSGGSPFSGLSSIAVRSGSYLDAIIIDGVHHGGSGGNLSPTFTFGSGEYISN $X_1$TIRSGDYIDNISF$X_2$TN$X_3$GRRFGPYGGSGGSANTLSNVKVIQINGX$_4$X$_5$GDYLDSLD X$_6$YYX$_7$QY (SEQ ID NO: 1), wherein $X_1$ can be M or V, $X_2$ can be E or Q, $X_3$ can be M, A, K, V, F, L, I, Q, R, or G, $X_4$ can be S or R, $X_5$ can be A or S, $X_6$ can be I or F, and $X_7$ can be E or Q provided that SEQ ID NO: 1 does not comprise the amino acid sequence of SEQ ID NO: 2.

In a first embodiment, the griffithsin mutant polypeptide comprises, consists essentially of, or consists of the amino acid sequence of SEQ ID NO: 3 (corresponding to the dVQK mutant). The amino acid sequence of SEQ ID NO: 3 corresponds to the amino acid sequence of SEQ ID NO: 1, wherein $X_1$, $X_2$, $X_3$, $X_4$, $X_5$, $X_6$, and $X_7$ of SEQ ID NO: 1 are V, Q, K, S, A, I, and E, respectively.

In a second embodiment, the griffithsin mutant polypeptide comprises, consists essentially of, or consists of the amino acid sequence of SEQ ID NO: 5 (corresponding to the dVQKR mutant). The amino acid sequence of SEQ ID NO: 5 corresponds to the amino acid sequence of SEQ ID NO: 1, wherein $X_1$, $X_2$, $X_3$, $X_4$, $X_5$, $X_6$, and $X_7$ of SEQ ID NO: 1 are V, Q, K, R, A, I, and E, respectively.

In a third embodiment, the griffithsin mutant polypeptide comprises, consists essentially of, or consists of the amino acid sequence of SEQ ID NO: 7 (corresponding to the dVQKFQ mutant). The amino acid sequence of SEQ ID NO: 7 corresponds to the amino acid sequence of SEQ ID NO: 1, wherein $X_1$, $X_2$, $X_3$, $X_4$, $X_5$, $X_6$, and $X_7$ of SEQ ID NO: 1 are V, Q, K, S, A, F, and Q, respectively.

In a fourth embodiment, the griffithsin mutant polypeptide comprises, consists essentially of, or consists of the amino acid sequence of SEQ ID NO: 9 (corresponding to the dQKR mutant). The amino acid sequence of SEQ ID NO: 9 corresponds to the amino acid sequence of SEQ ID NO: 1, wherein $X_1$, $X_2$, $X_3$, $X_4$, $X_5$, $X_6$, and $X_7$ of SEQ ID NO: 1 are M, Q, K, R, A, I, and E, respectively.

In additional embodiments, the griffithsin mutant polypeptide comprises, consists essentially of, or consists of:
 (i) the amino acid sequence of SEQ ID NO: 1, wherein $X_1$, $X_2$, $X_3$, $X_4$, $X_5$, $X_6$, and $X_7$ are M, Q, K/V/A, S, A, I, and E, respectively (corresponding to SEQ ID NO: 11);
 (ii) the amino acid sequence of SEQ ID NO: 1, wherein $X_1$, $X_2$, $X_3$, $X_4$, $X_5$, $X_6$, and $X_7$ are M, Q, K, S, A, I, and Q, respectively (corresponding to SEQ ID NO: 12);
 (iii) the amino acid sequence of SEQ ID NO: 1, wherein $X_1$, $X_2$, $X_3$, $X_4$, $X_5$, $X_6$, and $X_7$ are V, Q, K, S, A, I and Q, respectively (corresponding to SEQ ID NO: 13); or
 (iv) the amino acid sequence of SEQ ID NO: 1, wherein $X_1$, $X_2$, $X_3$, $X_4$, $X_5$, $X_6$, and $X_7$ are M, Q, K, S, A, F, and Q, respectively (corresponding to SEQ ID NO: 14).

The isoelectric points of several griffithsin mutant polypeptides are set forth in the following table.

TABLE 1

| Mutations | SEQ ID NO | pI |
|---|---|---|
| None (wild-type) | 2 | 5.73 |
| M61V, E75Q, M78K | 3 | 6.77 |
| M61V, E75Q, M78K, S106R | 5 | 7.47 |
| M61V, E75Q, M78K, I116F, E119Q | 7 | 7.47 |
| E75Q, M78K, S106R | 9 | 7.47 |
| E75Q, M78K/V/A | 11 | 6.77 |
| E75Q, M78K, E119Q | 12 | 7.47 |
| E75Q, M61V, M78K, E119Q | 13 | 7.47 |
| E75Q, M61V, M78K, I116F, E119Q | 14 | 7.47 |

If desired, the griffithsin mutant polypeptides of the invention (including antiviral fragments, fusion proteins, constructs, and conjugates) can be modified, for instance, by glycosylation, amidation, carboxylation, or phosphorylation, or by the creation of acid addition salts, amides, esters, in particular C-terminal esters, and N-acyl derivatives of the proteins of the invention. The polypeptides also can be modified to create protein derivatives by forming covalent or noncovalent complexes with other moieties in accordance with methods known in the art. Covalently-bound complexes can be prepared by linking the chemical moieties to functional groups on the side chains of amino acids comprising the proteins, or at the N- or C-terminus. Desirably, such modifications and conjugations do not adversely affect the activity of the polypeptides. While such modifications and conjugations can have greater or lesser activity, the activity desirably is not negated and is characteristic of the unaltered polypeptide.

The griffithsin mutant polypeptides can contain additional insertions, deletions, substitutions, or additions. However, in a preferred embodiment, the griffithsin mutant polypeptides form dimers like wild-type griffithsin. In other words, the changes to the wild-type griffithsin amino acid sequence do not result in the loss of the ability of the griffithsin mutant polypeptides to form dimers (i.e., monomeric griffithsin). Griffithsin dimers have been reported to have increased potency (e.g., about 1000 times increased potency) when compared to griffithsin monomers (Moulaei et al. *Structure*, 18(9): 1104-1115 (2010)). Therefore, in a preferred embodiment, the griffithsin mutant polypeptides do not contain a substitution at Leu2 (e.g., Leu2Ser) relative to the amino acid sequence of griffithsin (SEQ ID NO: 2) and/or an insertion of two or more residues between Ser16 and Gly17 (e.g., $(Gly-Ser)_n$, wherein n is 1 or 2) relative to the amino acid sequence of griffithsin (SEQ ID NO: 2) without compensating mutations/insertions that would allow for multimeric versions of griffithsin monomers in sequence (i.e., griffithsin tandemers). Although not wishing to be bound by any particular theory, the L2S and $(Gly-Ser)_n$ mutations are believed to be related to obligate monomeric griffithsin structures. Additionally or alternatively, the griffithsin mutant polypeptides can include N-terminal modifications, such as N-aceytlation (e.g., an N-terminal serine acetylated on the amino group). N-acetylation increases stability of aminopeptidases (O'Keefe et al., *Proc. Natl. Acad. Sci. U.S.A.*, 106(15): 6099-6104 (2009)).

The polypeptides (and fragments, fusion proteins, and constructs) can be prepared by any of a number of conventional techniques. The polypeptide can be isolated or purified from a recombinant source. For instance, a DNA fragment encoding a desired polypeptide can be subcloned into an appropriate vector using well-known molecular genetic techniques. The fragment can be transcribed and the polypeptide subsequently translated in vitro. Commercially available kits also can be employed. The polymerase chain reaction optionally can be employed in the manipulation of nucleic acids.

Such polypeptides also can be synthesized using an automated peptide synthesizer in accordance with methods known in the art. Alternately, the polypeptide (and fragments, fusion proteins, and constructs) can be synthesized using standard peptide synthesizing techniques well-known to those of skill in the art (e.g., as summarized in Bodanszky, *Principles of Peptide Synthesis*, (Springer-Verlag, Heidelberg: 1984)). In particular, the polypeptide can be synthesized using the procedure of solid-phase synthesis (see, e.g., Merrifield, *J. Am. Chem. Soc.*, 85: 2149-54 (1963); Barany et al., *Int. J. Peptide Protein Res.*, 30: 705-739 (1987); and U.S. Pat. No. 5,424,398). If desired, this can be done using an automated peptide synthesizer. Removal of the t-butyloxycarbonyl (t-BOC) or 9-fluorenylmethyloxycarbonyl (Fmoc) amino acid blocking groups and separation of the polypeptide from the resin can be accomplished by, for example, acid treatment at reduced temperature. The protein-containing mixture then can be extracted, for instance, with diethyl ether, to remove non-peptidic organic compounds, and the synthesized polypeptide can be extracted from the resin powder (e.g., with about 25% w/v acetic acid). Following the synthesis of the polypeptide, further purification (e.g., using HPLC) optionally can be performed in order to eliminate any incomplete proteins, polypeptides, peptides or free amino acids. Amino acid and/or HPLC analysis can be performed on the synthesized polypeptide to validate its identity.

For other applications according to the invention, it may be preferable to produce the polypeptide as part of a larger fusion protein, either by chemical conjugation or through genetic means, such as are known to those skilled in the art.

In this regard, the invention also provides a fusion protein comprising the griffithsin mutant polypeptide (or fragment thereof) and one or more other protein(s) having any desired properties or effector functions, such as cytotoxic or immunological properties, or other desired properties, such as to facilitate isolation, purification, analysis, or stability of the fusion protein.

A conjugate comprising the griffithsin mutant polypeptide coupled to at least one effector component, which can be the same or different, is also provided. The effector component can be polyethylene glycol, dextran, albumin, an immunological reagent, a toxin, an antiviral agent, or a solid support matrix. "Immunological reagent" includes, but is not limited to, an antibody, an antibody fragment (e.g., an F(ab')$_2$, an Fab', an Fab, an Fv, an scFv, a dsFv, an eAd, or an Fc antibody fragment), an immunoglobulin, and an immunological recognition element. An immunological recognition element is an element, such as a peptide, e.g., the FLAG sequence of a recombinant griffithsin mutant polypeptide-FLAG fusion protein, which facilitates, through immunological recognition, isolation and/or purification and/or analysis of the protein or peptide to which it is attached. An immunological reagent also can be an immunogenic peptide, which can be fused to the griffithsin mutant polypeptide for enhancing an immune response.

In this respect, the invention provides an antiviral conjugate comprising the griffithsin mutant polypeptide or fragment thereof bound to a virus or viral envelope glycoprotein. The griffithsin mutant polypeptide fusion protein is a type of griffithsin mutant polypeptide conjugate, wherein the griffithsin mutant polypeptide is coupled to one or more other protein(s) having any desired properties or effector functions, such as cytotoxic or immunological properties, or other desired properties, such as to facilitate isolation, purification or analysis of the fusion protein or increase the stability or in vivo half-life of the fusion protein. The griffithsin mutant polypeptide also can be attached to a chemical moiety which allows recognition, isolation, purification, and/or analysis of the protein or peptide. An example of such a chemical moiety is a His tag.

A "toxin" can be, for example, *Pseudomonas* exotoxin. An "antiviral agent" can be AZT, ddI, ddC, 3TC gancyclovir, fluorinated dideoxynucleosides, nevirapine, R82913, Ro 31-8959, BI-RJ-70, acyclovir, α-interferon, recombinant sCD4, michellamines, calanolides, nonoxynol-9, gossypol and derivatives thereof, gramicidin, amantatadine, rimantadine, and neuraminidase inhibitors, cyanovirin-N or a functional homolog or derivative thereof (see, for example, U.S. Pat. No. 5,843,882), or scytovirin or a functional homolog or derivative thereof (see, e.g., U.S. Pat. Nos. 7,494,798 and 8,067,530). A "solid support matrix" can be a magnetic bead, a flow-through matrix, a sponge, a stent, a culture plate, or a matrix comprising a contraceptive device, such as a condom, diaphragm, cervical cap, vaginal ring or contraceptive sponge. In an alternative embodiment, a solid support matrix can be an implant for surgical implantation in a host and, if appropriate, later removal.

Conjugates furthermore can comprise the griffithsin mutant polypeptides coupled to more than one effector molecule, each of which, optionally, can have different effector functions (e.g., such as a toxin molecule (or an immunological reagent) and a polyethylene glycol (or dextran or albumin) molecule). Diverse applications and uses of functional proteins and peptides attached to or immobilized on a solid support matrix, are exemplified more specifically for poly(ethylene glycol) conjugated proteins or peptides in a review by Holmberg et al. (In *Poly(Ethylene Glycol) Chemistry: Biotechnical and Biomedical Applications*, Harris, ed., Plenum Press: New York (1992), pp. 303-324).

The invention also provides a nucleic acid molecule that encodes the griffithsin mutant polypeptide or fusion protein thereof. For example, the invention provides a nucleic acid molecule comprising the nucleotide sequence of SEQ ID NO: 4, 6, 8, or 10.

Using an appropriate nucleic acid (e.g., DNA) coding sequence, the inventive griffithsin mutant polypeptides, fusion proteins, constructs, and conjugates can be made by genetic engineering techniques (for general background see, e.g., Nicholl, in *An Introduction to Genetic Engineering*, Cambridge University Press: Cambridge (1994), pp. 1-5 & 127-130; Steinberg et al., in *Recombinant DNA Technology Concepts and Biomedical Applications*, Prentice Hall: Englewood Cliffs, N.J. (1993), pp. 81-124 & 150-162; Sofer in *Introduction to Genetic Engineering*, Butterworth-Heinemann, Stoneham, Mass. (1991), pp. 1-21 & 103-126; Old et al., in *Principles of Gene Manipulation*, Blackwell Scientific Publishers: London (1992), pp. 1-13 & 108-221; and Emtage, in *Delivery Systems for Peptide Drugs*, Davis et al., eds., Plenum Press: New York (1986), pp. 23-33). For example, DNA encoding the inventive griffithsin mutant polypeptides, fusion proteins, constructs, and conjugates can be incorporated into an appropriate expression vector and delivered into an appropriate polypeptide-synthesizing organism (e.g., *E. coli, S. cerevisiae, P. pastoris*, or other bacterial, yeast, insect, plant or mammalian cells), where the DNA, under the control of an endogenous or exogenous promoter, can be appropriately transcribed and translated. Alternatively, the expression vector can be administered to a plant or animal, for example, for large-scale production (see, e.g., Fischer et al., *Transgenic Res.*, 9(4-5): 279-299 (2000); Fischer et al., *J. Biol. Regul. Homeost. Agents*, 14: 83-92 (2000); deWilde et al., *Plant Molec. Biol.*, 43: 347-359 (2000); Houdebine, *Transgenic Research*, 9: 305-320 (2000); Brink et al., *Theriogenology*, 53: 139-148 (2000); Pollock et al., *J. Immunol. Methods*, 231: 147-157 (1999); Conrad et al., *Plant Molec. Biol.*, 38: 101-109 (1998); Staub et al., *Nature Biotech.*, 18: 333-338 (2000); McCormick et al., *PNAS USA*, 96: 703-708 (1999); Zeitlin et al., *Nature Biotech.*, 16: 1361-1364 (1998); Tacker et al., *Microbes and Infection*, 1: 777-783 (1999); Tacket et al., *Nature Med.*, 4(5): 607-609 (1998); and *Methods in Biotechnology, Recombinant Proteins from Plants, Production and Isolation of Clinically Useful Compounds*, Cunningham and Porter, eds., Humana Press: Totowa, N.J. (1998)). Such expression vectors (including, but not limited to, phage, cosmid, viral, and plasmid vectors) are known to those skilled in the art, as are reagents and techniques appropriate for gene transfer (e.g., transfection, electroporation, transduction, micro-injection, transformation, etc.). If the griffithsin mutant polypeptides are to be recombinantly produced in isolated eukaryotic cells or in a eukaryotic organism, such as a plant (see above references and also *Methods in Biotechnology, Recombinant Proteins from Plants, Production and Isolation of Clinically Useful Compounds*, Cunningham and Porter, eds., Humana Press: Totowa, N.J. (1998)), any glycosylation sites in the polypeptides are rendered glycosylation resistant (e.g., the N-linked glycosylation sites at positions 45, 60, 71, and/or 104 relative to the amino acid sequence of griffitshsin (SEQ ID NO: 2). Subsequently, the recombinantly produced polypeptide can be isolated and purified using standard techniques known in the art (e.g., chromatography, centrifugation, differential solubility, isoelectric focusing, etc.), and assayed for antiviral activity.

In this regard, the invention provides a vector comprising the nucleic acid molecule that encodes the griffithsin mutant polypeptide, fusion protein, or construct. The vector can be targeted to a cell-surface receptor if so desired. A nucleic acid molecule as described above can be cloned into any suitable vector and can be used to transform or transfect any suitable host. The selection of vectors and methods to construct them are commonly known to persons of ordinary skill in the art and are described in general technical references. Desirably, the vector comprises regulatory sequences, such as transcription and translation initiation and termination codons, which are specific to the type of host (e.g., bacterium, fungus, plant or animal) into which the vector is to be introduced, as appropriate and taking into consideration whether the vector is DNA or RNA. Preferably, the vector comprises regulatory sequences that are specific to the genus of the host. Most preferably, the vector comprises regulatory sequences that are specific to the species of the host.

Vector constructs, which are circular or linear, can be prepared to contain an entire nucleic acid molecule as described above or a portion thereof ligated to a replication system functional in a prokaryotic or eukaryotic host cell. Replication systems can be derived from ColE1, 2 mμ plasmid, λ, SV40, bovine papilloma virus, and the like.

In addition to the replication system and the inserted nucleic acid, the vector constructs can include one or more marker genes, which allow for selection of transformed or transfected hosts. Marker genes include biocide resistance, e.g., resistance to antibiotics, heavy metals, etc., complementation in an auxotrophic host to provide prototrophy, and the like.

One of ordinary skill in the art will appreciate that any of a number of vectors known in the art are suitable for use in the invention. Suitable vectors include those designed for propagation and expansion or for expression or both. Examples of suitable vectors include, for instance, plasmids, plasmid-liposome complexes, and viral vectors, e.g., poxviral vectors, parvoviral-based vectors (i.e., adeno-associated virus (AAV)-based vectors), retroviral vectors, herpes simplex virus (HSV)-based vectors, and adenovirus-based vectors. Any of these expression constructs can be prepared using standard recombinant DNA techniques described in, e.g., Sambrook et al., *Molecular Cloning: A Laboratory Manual*, 2$^{nd}$ edition, Cold Spring Harbor Laboratory Press, Cold Spring Harbor, N.Y. (1989); Ausubel et al., *Current Protocols in Molecular Biology*, Greene Publishing Associates and John Wiley & Sons, New York, N.Y. (1994); Fischer et al., *Transgenic Res.*, 9(4-5): 279-299 (2000); Fischer et al., *J. Biol. Regul. Homeost. Agents*, 14: 83-92 (2000); deWilde et al., *Plant Molec. Biol.*, 43: 347-359 (2000); Houdebine, *Transgenic Research*, 9: 305-320 (2000); Brink et al., *Theriogenology*, 53: 139-148 (2000); Pollock et al., *J. Immunol. Methods*, 231: 147-157 (1999); Conrad et al., *Plant Molec. Biol.*, 38: 101-109 (1998); Staub et al., *Nature Biotech.*, 18: 333-338 (2000); McCormick et al., *PNAS USA*, 96: 703-708 (1999); Zeitlin et al., *Nature Biotech.*, 16: 1361-1364 (1998); Tacker et al., *Microbes and Infection*, 1: 777-783 (1999); and Tacket et al., *Nature Med.*, 4(5): 607-609 (1998). Examples of cloning vectors include the pUC series, the pBluescript series (Stratagene, LaJolla, Calif.), the pET series (Novagen, Madison, Wis.), the pGEX series (Pharmacia Biotech, Uppsala, Sweden), and the pEX series (Clonetech, Palo Alto, Calif.). Bacteriophage vectors, such as λGT10, λGT11, λZapII (Stratagene), λEMBL4, and λNM1149, also can be used. Examples of plant expression vectors include pBI101, pBI101.2, pBI101.3, pBI121 and pBIN19 (Clonetech, Palo Alto, Calif.). Examples of animal expression vectors include pEUK-C1, pMAM and pMAMneo (Clonetech). When the vector is a plasmid (e.g. DNA plasmid), the plasmid can be complexed with chitosan.

When the vector is for administration to a host (e.g., human), the vector preferably has a low replicative efficiency in a target cell (e.g., no more than about 1 progeny per cell or, more preferably, no more than 0.1 progeny per cell are produced). Replication efficiency can readily be determined empirically by determining the virus titer after infection of the target cell.

An expression vector can comprise a native or nonnative promoter operably linked to the nucleic acid molecule. The selection of promoters, e.g., strong, weak, inducible, tissue-specific and developmental-specific, is within the skill in the art. Similarly, the combining of a nucleic acid molecule as described above with a promoter is also within the skill in the art.

The nucleic acid molecule can be subcloned as part of a gene fusion. In a transcriptional gene fusion, the DNA or cDNA will contain its own control sequence directing appropriate production of protein (e.g., ribosome binding site, translation initiation codon, etc.), and the transcriptional control sequences (e.g., promoter elements and/or enhancers) will be provided by the vector. In a translational gene fusion, transcriptional control sequences as well as at least some of the translational control sequences (i.e., the translational initiation codon) will be provided by the vector. In the case of a translational gene fusion, a chimeric protein will be produced.

Nucleic acid molecules also can be constructed for specific fusion proteins containing the griffithsin mutant polypeptide plus a fusion component conferring additional desired attribute(s) to the composite protein. For example, a fusion sequence for a toxin or immunological reagent can be added to facilitate purification and analysis of the functional protein.

Nucleic acid molecules (e.g., genes) can be specifically constructed to code for fusion proteins, which contain the griffithsin mutant polypeptide coupled to an effector protein, such as a toxin or immunological reagent, for specific targeting to a virus or viral-infected cells, e.g., HIV and/or HIV-infected cells. In these instances, the griffithsin mutant polypeptide construct serves not only as a neutralizing agent but also as a targeting agent to direct the effector activities of these molecules selectively against a given virus, such as HIV or influenza. Thus, for example, a therapeutic agent can be obtained by combining the HIV-targeting function or influenza-targeting function of a functional the griffithsin mutant polypeptide with a toxin aimed at neutralizing infectious virus and/or by destroying cells producing infectious virus, such as HIV or influenza. Similarly, a therapeutic agent can be obtained, which combines the viral-targeting function of the griffithsin mutant polypeptide with the multivalency and effector functions of various immunoglobulin subclasses.

Viral-targeted conjugates can be prepared either by genetic engineering techniques or by chemical coupling of the targeting component with an effector component. The most feasible or appropriate technique to be used to construct a conjugate or fusion protein comprising the griffithsin mutant polypeptide will be selected based upon consideration of the characteristics of the particular effector molecule selected for coupling to the griffithsin mutant polypeptide. For example, with a selected non-proteinaceous effector molecule, chemical coupling, rather than genetic engineering techniques, may be the only feasible option for creating the desired conjugate.

An isolated cell comprising the griffithsin mutant polypeptide, fusion protein, construct, conjugate, nucleic acid molecule, or vector is also provided. Any suitable cell can be used. Examples include host cells, such as *E. coli* (e.g., *E. coli* Tb-1, TG-2, DH5a, XL-Blue MRF' (Stratagene), SA2821, and Y1090), *Bacillus subtilis, Salmonella typhimurium, Serratia marcescens, Pseudomonas* (e.g., *P. aerugenosa*), *N. grassa*, insect cells (e.g., Sf9, Ea4), yeast (*S. cerevisiae*) cells, and cells derived from a mammal, including human cell lines. Specific examples of suitable eukaryotic cells include VERO, HeLa, 3T3, Chinese hamster ovary (CHO) cells, W138 BHK, COS-7, and MDCK cells. Alternatively and preferably, cells from a mammal, such as a human, to be treated in accordance with the methods described herein can be used as host cells. In one embodiment, the cell is a human B cell.

The cell can be a mammalian cell, bacterium, or yeast. A preferred bacterium is lactobacillus or other commensal microorganism. The above-described nucleic acid molecule, optionally in the form of a vector, can be introduced into a host cell using such techniques as calcium chloride-mediated transformation, transduction, conjugation, triparental mating, DEAE, dextran-mediated transfection, infection, membrane fusion with liposomes, high velocity bombardment with DNA-coated microprojectiles, direct microinjection into single cells, and electroporation. Desirably, the cell comprising the vector or nucleic acid expresses the griffithsin mutant polypeptide, fusion protein, or conjugate such that the nucleic acid sequence is transcribed and translated efficiently by the cell.

The invention further provides a composition comprising (i) the griffithsin mutant polypeptide, fusion protein, construct, conjugate, nucleic acid molecule, vector, or cell and (ii) a carrier, excipient or adjuvant therefor. Preferably, component (i) of the composition is present in an antiviral effective amount and the carrier is pharmaceutically acceptable. By "antiviral effective amount" is meant an amount sufficient to inhibit the infectivity of the virus.

The carrier can be any of those conventionally used and is limited only by chemico-physical considerations, such as solubility and lack of reactivity with the active agent of the invention, and by the route of administration. It is preferred that the pharmaceutically acceptable carrier be one which is chemically inert to the active agent and one which has no detrimental side effects or toxicity under the conditions of use. The pharmaceutically acceptable carriers described herein, for example, vehicles, adjuvants, excipients, and diluents, are well-known to those ordinarily skilled in the art and are readily available to the public. Typically, the composition, such as a pharmaceutical composition, can comprise a physiological saline solution; dextrose or other saccharide solution; or ethylene, propylene, polyethylene, or other glycol. The pharmaceutical composition preferably does not comprise mannose or N-acetyl-glucosamine, as these molecules may interfere with the functioning of the active agent. Additionally, the pharmaceutical composition preferably does not comprise glucose, since griffithsin binding to gp120 is somewhat inhibited by glucose (Mori et al., *J. Biol. Chem.*, 280(10): 9345-9353 (2005)).

If the composition is to be used to induce an immune response, it comprises an immune response-inducing amount of the griffithsin mutant polypeptide, fusion protein, construct, conjugate, nucleic acid molecule, vector, or cell and can further comprise an immunoadjuvant, such as polyphosphazene polyelectrolyte.

The composition can further comprise at least one additional active agent, such as an antiviral agent, in an antiviral effective amount. Suitable antiviral agents include AZT, ddA, ddI, ddC, 3TC gancyclovir, fluorinated dideoxynucleosides, acyclovir, α-interferon, nonnucleoside analog compounds, such as nevirapine (Shih et al., *PNAS*, 88: 9878-9882, (1991)), TIBO derivatives, such as R82913 (White et al., *Antiviral Res.*, 16: 257-266 (1991)), Ro31-8959, BI-RJ-70 (Merigan, *Am. J. Med.*, 90 (Suppl.4A): 8S-17S (1991)), michellamines (Boyd et al., *J. Med. Chem.*, 37: 1740-1745 (1994)) and calanolides (Kashman et al., *J. Med. Chem.*, 35: 2735-2743 (1992)), nonoxynol-9, gossypol and derivatives, gramicidin, Enfurtide (i.e., T20), cyanovirin-N and functional homologs thereof (Boyd et al. (1997), supra and U.S. Pat. No. 5,843,882), or scytovirin or a functional homolog or derivative thereof (see, e.g., U.S. Pat. Nos. 7,494,798 and 8,067,530). Other exemplary antiviral compounds include protease inhibitors (see R. C. Ogden and C. W. Flexner, eds., *Protease Inhibitors in AIDS Therapy*, Marcel Dekker, N.Y. (2001)), such as saquinavir (see I. B. Duncan and S. Redshaw, in R. C. Ogden and C. W. Flexner, supra, pp. 27-48), ritonavir (see D. J. Kempf, in R. C. Ogden and C. W. Flexner, supra, pp. 49-64), indinavir (see B. D. Dorsey and J. P. Vacca, in R. C. Ogden and C. W. Flexner, supra, pp. 65-84), nelfinavir (see S. H. Reich, in R. C. Ogden and C. W. Flexner, supra, pp. 85-100), amprenavir (see R. D. Tung, in R. C. Ogden and C. W. Flexner, supra, pp. 101-118), tenofovir (see Ferir et al., *Virology*, 417(2): 253-258 (2011)), maraviroc (see Ferir et al., *Virology*, 417(2): 253-258 (2011)), carbohydrate binding agents (see Ferir et al., *AIDS Res. Hum. Retrovir.*, 28(11): 1513-23 (2012)), carrageenan, and anti-TAT agents. If the composition is to be used to induce an immune response, it comprises an immune response-inducing amount of the inventive agent and can further comprise an immunoadjuvant, such as polyphosphazene polyelectrolyte.

The composition (e.g., pharmaceutical composition) can contain other pharmaceuticals, such as virucides, immunomodulators, immunostimulants, antibiotics and absorption enhancers. Exemplary immunomodulators and immunostimulants include various interleukins, sCD4, cytokines, antibody preparations, blood transfusions, and cell transfusions. Exemplary antibiotics include antifungal agents, antibacterial agents, and anti-*Pneumocystitis carnii* agents. Exemplary absorption enhancers include bile salts and other surfactants, saponins, cyclodextrins, and phospholipids.

The mGRFT tandem construct, fusion protein, construct, conjugate, nucleic acid molecule, vector, cell, or composition can be used to inhibit a broad range of viruses (see, e.g., *Principles of Virology: Molecular Biology, Pathogenesis, and Control*, Flint et al., eds., ASM Press: Washington, D.C. (2000), particularly Chapter 19). Examples of viruses that may be treated in accordance with the invention include, but are not limited to, Type C and Type D retroviruses, HTLV-1, HTLV-2, HIV, FIV, FLV, SIV, MLV, BLV, BIV, equine infectious virus, anemia virus, Japanese encephalitis (see, e.g., Ishag et al, *Arch. Virol.*, 158(2): 349-58 (2013)), avian sarcoma viruses, such as Rous sarcoma virus (RSV), hepatitis type A, B, C, non-A and non-B viruses, arboviruses, varicella viruses, herpes viruses (e.g., HHV-6, HSV-1, and HSV-2 (see, e.g., Nixon et al., *J. Virol.*, 87(12): doi: 10.1128/JVI.00012-13 (2013)), measles, mumps, Filovirus (e.g., Ebola, such as Ebola strains Sudan, Zaire, Cote d'Ivoire, and Reston), human and animal coronavirus (e.g., SARS virus, MERS virus) (O'Keefe et al., *J. Virol.*, 84(5): 2511-2521

(2010)), Nipah virus, and rubella viruses. The inventive mGRFT tandem construct, fusion protein, construct, conjugate, nucleic acid molecule, vector, or cell also can be used to inhibit influenza viral infection, such as an H5N1 viral infection, i.e., a Bird flu viral infection, (see, e.g., *Fields Virology*, third edition, Fields et al., eds., Lippincott-Raven Publishers: Philadelphia, Pa. (1996), particularly Chapter 45) prophylactically and therapeutically in accordance with the methods set forth herein. Additionally, the mGRFT tandem construct, fusion protein, construct, conjugate, nucleic acid molecule, vector, cell, or composition can be used to inhibit parasites, such as Trichomonas vaginalis.

The griffithsin mutant polypeptide, fusion protein, construct, conjugate, nucleic acid molecule, vector, cell, or composition thereof can be administered to any host (e.g., mammal, preferably a human) in need thereof. As a result of administration of griffithsin mutant polypeptide, fusion protein, construct, conjugate, nucleic acid molecule, vector, or cell to the mammal, infection of the mammal by a virus (e.g., HIV) is inhibited. The inventive method can prophylactically or therapeutically inhibit infection by any type of virus (e.g., HIV), but preferably inhibits an HIV infection, such as an HIV-1 and/or HIV-2 infection. The inventive method can be used to inhibit infection by any HIV group (e.g., groups M and/or O), and subtype (e.g., clades A, B, C, D, E, EA, F, and/or G).

When provided therapeutically, the griffithsin mutant polypeptide, fusion protein, construct, conjugate, nucleic acid molecule, vector, cell or composition thereof is provided at or after the diagnosis of a viral (e.g., HIV) infection.

When provided prophylactically (e.g., as a topical microbicide agent in the form of a film or solid suppository), the griffithsin mutant polypeptide, fusion protein, construct, conjugate, nucleic acid molecule, vector, cell or composition thereof is provided in advance of a viral (e.g., HIV) infection, such as to patients or subjects who are at risk for being exposed to a virus (e.g., HIV) or who have been newly exposed to a virus (e.g., HIV). If the virus is HIV, then the patients or subjects include healthcare workers, fetuses, neonates, or infants (e.g., nursing infants) whose mothers are infected or at risk for being infected, intravenous drug users, recipients of blood transfusions, blood products, or transplantation tissue, and other individuals who have been exposed to a body fluid that contains or may contain HIV. The prophylactic administration of the griffithsin mutant polypeptide, fusion protein, construct, conjugate, nucleic acid molecule, vector, or cell or composition thereof prevents, ameliorates, or delays viral (e.g., HIV) infection. In subjects who have been newly exposed to the virus but who have not yet displayed the presence of the virus (as measured by PCR or other assays for detecting the virus) in blood or other body fluid, efficacious treatment with the griffithsin mutant polypeptide, fusion protein, construct, conjugate, nucleic acid molecule, vector, or cell or composition thereof partially or completely inhibits or delays the appearance of the virus or minimizes the level of the virus in the blood or other body fluid of the exposed individual.

The invention provides a method of inhibiting prophylactically or therapeutically a viral infection, in particular an influenza viral infection, an HIV infection, or a coronavirus (e.g., SERS or MERS) infection, of a host. The method comprises administering to the host an effective amount of the griffithsin mutant polypeptide, fusion protein, construct, conjugate, nucleic acid molecule, vector, or cell or composition thereof (herein referred to as "the inventive antiviral agent"). When the viral infection is an influenza viral infection and the inventive antiviral agent is administered topically to the host, preferably the inventive antiviral agent is administered to the respiratory system of the host, preferably as an aerosol or microparticulate powder.

The prophylactic and therapeutic treatment of many viral infections, including influenza virus infections, is complicated by appearance of virus forms resistant to currently employed medications, such as neurominidase inhibitors. The inventive method is particularly useful in this context, as the inventive antiviral agent binds a wide range of glycoproteins present on the viral surface. Accordingly, the inventive antiviral agent can be administered to an animal, preferably a human, dog, cat, bird, cow, pig, horse, lamb, mouse, or rat, in combination with other antiviral agents to guard against the propagation of antiviral-resistant strains of virus. In addition, it is thought that during adaptive mutation (e.g., resistance to neuraminidase inhibitors), the level of glycosylation found at the viral surface increases in some viruses, such as influenza. Thus, in that the inventive antiviral agent binds sugars of viral surface glycoproteins, the inventive method provides a valuable complimentary therapy to current antiviral regimens.

One skilled in the art will appreciate that various routes of administering a drug are available, and, although more than one route can be used to administer a particular drug, a particular route can provide a more immediate and more effective reaction than another route. For example, the antiviral agent of the invention can be inhaled in methods of prophylactically treating a subject for influenza infection. Delivery of the antiviral agent to a location of initial viral contact, such as the nose or mouth, blocks the onset of infection. The antiviral agent can be administered via subcutaneous injection. Alternatively, in acute or critical medical situations, the antiviral agent can be administered intravenously. In many cases of infection, a patient generates an immune response to a virus. However, the effects of the viral infection so severely compromise the health of the patient that an effective immune response is not reached prior to death. Administration of the antiviral agent can prolong the life of the patient until a patient's natural immune defense clears the virus.

Formulations suitable for oral administration can consist of liquid solutions, such as an effective amount of the compound dissolved in diluents, such as water, saline, or fruit juice; capsules, sachets or tablets, each containing a predetermined amount of the active ingredient, as solid, granules or freeze-dried cells; solutions or suspensions in an aqueous liquid; and oil-in-water emulsions or water-in-oil emulsions. Tablet forms can include one or more of lactose, mannitol, corn starch, potato starch, microcrystalline cellulose, acacia, gelatin, colloidal silicon dioxide, croscarmellose sodium, talc, magnesium stearate, stearic acid, and other excipients, colorants, diluents, buffering agents, moistening agents, preservatives, flavoring agents, and pharmacologically compatible carriers. Suitable formulations for oral delivery can also be incorporated into synthetic and natural polymeric microspheres, or other means to protect the agents of the present invention from degradation within the gastrointestinal tract (see, for example, Wallace et al., *Science*, 260: 912-915 (1993)).

The antiviral agent of the invention, alone or in combination with other antiviral compounds, can be made into aerosol formulations or microparticulate powder formulations to be administered via inhalation. These aerosol formulations can be placed into pressurized acceptable propellants, such as dichlorodifluoromethane, propane, nitrogen, and the like.

The antiviral agent of the invention, alone or in combinations with other antiviral compounds or absorption modulators, can be made into suitable formulations for transdermal application and absorption, such as a patch (Wallace et al. (1993), supra). Transdeinial electroporation or iontophoresis also can be used to promote and/or control the systemic delivery of the compounds and/or compositions of the present invention through the skin (e.g., see Theiss et al., *Meth. Find. Exp. Clin. Pharmacol.*, 13: 353-359 (1991)).

Formulations suitable for topical administration include lozenges comprising the active ingredient in a flavor, usually sucrose and acacia or tragacanth; pastilles comprising the active ingredient in an inert base, such as gelatin and glycerin, or sucrose and acacia; and mouthwashes comprising the active ingredient in a suitable liquid carrier; as well as creams, emulsions, gels and the like containing, in addition to the active ingredient, such as, for example, freeze-dried lactobacilli or live lactobacillus cultures genetically engineered to directly produce a construct, fusion protein, or conjugate of the present invention, such carriers as are known in the art. Topical administration is preferred for the prophylactic and therapeutic treatment of influenza viral infection, such as through the use of an inhaler, for example.

Formulations for rectal administration can be presented, for example, as a film formulation or suppository with a suitable base comprising, for example, cocoa butter or a salicylate. Formulations suitable for vaginal administration can be presented as film formulations (solid films), vaginal ring formulations (intravaginal rings), pessaries, tampons, creams, gels, pastes, foams, or spray formulas containing, in addition to the active ingredient, such as, for example, freeze-dried lactobacilli or live lactobacillus cultures genetically engineered to directly produce a construct, fusion protein, or conjugate of the present invention, such carriers as are known in the art to be appropriate. Similarly, the active ingredient can be combined with a lubricant as a coating on a condom. Indeed, preferably, the active ingredient is applied to any contraceptive device, including, but not limited to, a condom, a diaphragm, a cervical cap, a vaginal ring, and a sponge, wherein the device is not limited to administration as a contraceptive.

Formulations suitable for parenteral administration include aqueous and non-aqueous, isotonic sterile injection solutions, which can contain anti-oxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. The formulations can be presented in unit-dose or multi-dose sealed containers, such as ampules and vials, and can be stored in a freeze-dried (lyophilized) condition requiring only the addition of the sterile liquid carrier, for example, water, for injections, immediately prior to use. Extemporaneous injection solutions and suspensions can be prepared from sterile powders, granules, and tablets of the kind previously described.

Formulations comprising a construct, fusion protein, or conjugate suitable for virucidal (e.g., HIV) sterilization of inanimate objects, such as medical supplies or equipment, laboratory equipment and supplies, instruments, devices, and the like, can, for example, be selected or adapted as appropriate, by one skilled in the art, from any of the aforementioned compositions or formulations. In that respect, the invention provides a method of inhibiting a virus in a biological sample or in/on an inanimate object comprising contacting the biological sample or the inanimate object with a viral-inhibiting amount of the inventive construct, conjugate, nucleic acid, vector, cell, or composition, which method optionally further comprises the prior, simultaneous, or subsequent contacting of the biological sample or inanimate object with an antiviral agent or another agent that is efficacious in inhibiting the virus.

It will also be appreciated by one skilled in the art that a DNA sequence of the griffithsin mutant polypeptide, conjugate, construct, or fusion protein of the invention can be inserted ex vivo into mammalian cells previously removed from a given animal, in particular a human, host. Such cells can be employed to express the corresponding griffithsin mutant polypeptide, conjugate, construct, or fusion protein in vivo after reintroduction into the host. Feasibility of such a therapeutic strategy to deliver a therapeutic amount of an agent in close proximity to the desired target cells and pathogens, i.e., virus, more particularly retrovirus, specifically HIV and its envelope glycoprotein gp120, has been demonstrated in studies with cells engineered ex vivo to express sCD4.

It is also possible that, as an alternative to ex vivo insertion of the DNA sequence of the griffithsin mutant polypeptide, conjugate, construct, or fusion protein of the invention, such a sequence can be inserted into cells directly in vivo, such as by use of an appropriate viral vector. Such cells transfected in vivo are expected to produce antiviral amounts of the griffithsin mutant polypeptide, conjugate, construct, or fusion protein directly in vivo.

Alternatively, a DNA sequence corresponding to the griffithsin mutant polypeptide, conjugate, construct, or fusion protein can be inserted into suitable nonmammalian host cells, and such host cells will express therapeutic or prophylactic amounts of the griffithsin mutant polypeptide, conjugate, construct, or fusion protein directly in vivo within or onto a desired body compartment of an animal, in particular a human. In a preferred embodiment of the present invention, a method of female-controllable prophylaxis against viral infection, such as HIV infection, comprises the intravaginal administration and/or establishment of, in a female human, a persistent intravaginal population of lactobacilli that have been transformed with a coding sequence of the present invention to produce, over a prolonged time, effective virucidal levels of a the griffithsin mutant polypeptide, conjugate, or fusion protein, directly on or within or onto the vaginal and/or cervical and/or uterine mucosa.

One of ordinary skill can determine the effectiveness of the composition to inhibit a viral infection (e.g., by inducing an immune response against the virus) using routine methods known in the art. Cell-mediated response can be determined by employing, for example, a virus antigen-stimulated T-cell proliferation assay. The presence of a humoral immune response can be determined, for instance, with the Enzyme Linked Immunosorbent Assay (ELISA). The skilled artisan will appreciate that there are numerous other suitable assays for evaluating induction of an immune response. To the extent that a dose is inadequate to induce an appropriate immune response, "booster" administrations can subsequently be administered in order to prompt a more effective immune response.

The pre-binding of griffithsin to HIV gp120 envelope protein has been shown to increase the immunogenicity of the envelope glycoprotein when griffithsin and HIV gp120 envelope protein are administered as a vaccine (see, e.g., Banerjee et al, *AIDS Res. Hum. Retrovir.*, 28(2): 206-214 (2012)). Therefore, in one aspect of the invention, the griffithsin mutant polypeptide, fusion protein, construct, conjugate, nucleic acid molecule, vector, cell or composition thereof is administered with HIV gp120 envelope glycoprotein.

Since the effective level is used as the preferred endpoint for dosing, the actual dose and schedule can vary, depending upon interindividual differences in pharmacokinetics, drug distribution, and metabolism. The "effective level" can be defined, for example, as the blood or tissue level (e.g., 0.1-1000 nM) desired in the patient that corresponds to a concentration of the griffithsin mutant polypeptide, fusion protein, construct, conjugate, nucleic acid molecule, vector, cell, or composition thereof, which inhibits a virus, such as HIV, in an assay known to predict for clinical anti-viral activity of chemical compounds and biological agents. The "effective level" for agents of the invention also can vary when the griffithsin mutant polypeptide, fusion protein, construct, conjugate, nucleic acid molecule, vector, cell, or composition thereof, is used in combination with AZT or other known anti-viral compounds or combinations thereof.

One skilled in the art can easily determine the appropriate dose, schedule, and method of administration for the exact formulation of the composition being used, in order to achieve the desired effective concentration in the individual patient. One skilled in the art also can readily determine and use an appropriate indicator of the "effective concentration" of the griffithsin mutant polypeptide, fusion protein, construct, conjugate, nucleic acid molecule, vector, cell, or composition thereof of the invention by a direct (e.g., analytical chemical analysis) or indirect (e.g., with surrogate indicators such as p24 or RT) analysis of appropriate patient samples (e.g., blood and/or tissues).

The inventive methods can further comprise concurrent, pre- or post-treatment with an adjuvant to enhance the immune response, such as the prior, simultaneous or subsequent administration, by the same or a different route, of an antiviral agent or another agent that is efficacious in inducing an immune response to the virus, such as an immunostimulant.

The antiviral, e.g., anti-HIV, activity of the griffithsin mutant polypeptide, fusion protein, construct, conjugate, nucleic acid molecule, vector, cell or composition thereof of the invention can be further demonstrated in a series of interrelated in vitro anti-viral assays (Gulakowski et al., *J. Virol. Methods*, 33: 87-100 (1991)), which accurately predict for anti-viral activity in humans. These assays measure the ability of compounds to prevent the replication of HIV and/or the cytopathic effects of HIV on human target cells. These measurements directly correlate with the pathogenesis of HIV-induced disease in vivo.

The following examples further illustrate the invention but, of course, should not be construed as in any way limiting its scope.

Example 1

This example demonstrates the antiviral activity and thermal stability of the griffithsin mutants.

Griffithsin mutants were analyzed for their thermal stability by differential scanning calorimetry. The results are represented by the melting temperature (Tm) of each mutant. For comparison, the melting temperature of native griffithsin is ~81° C.

The anti-HIV activity of each griffithsin mutant also was evaluated in a live virus HIV-1RF assay system measuring the reduction of HIV-1-induced cytopathicity in CEM-SS T-lymphoblastic cells. The EC50 value refers to the effective concentration of the protein at which 50% of the cells are protected. Native griffithsin has a reported $EC_{50}$ value of ~0.05 nM in this same assay system.

TABLE 2

| Proteins | SEQ ID NO | Anti-HIV EC50 (nM) | DSC Tm (° C.) | DSC ΔH (kcal/mol) |
|---|---|---|---|---|
| M61V, E75Q, M78K, S106R | 5 | 0.63 | 72.83 | 172 |
| M61V, E75Q, M78K | 3 | 1.22 | 78.92 | 159 |
| M61V, E75Q, M78K, I116F, E119Q | 7 | 1.14 | 77.03 | 132 |

Example 2

This example demonstrates the results of differential light scattering (DLS).

This technique is used to determine the level of size dispersity of dissolved proteins in solution. It measures the percent polydispersity in each solution. The lower the percent polydispersity, the more soluble the protein in that solution. Ideally, a protein in solution will have a polydispersity percentage less than 15%.

Solutions of griffithsin mutants were taken up at high concentrations (>6 mg/ml) in solutions over a range of pH values to assess mutation effects on solubility. Of particular importance is the solubility at pH=5 as this is close to normal vaginal pH. Griffithsin mutants that are more soluble at the indicated pHs will be more bioavailable at those pHs in physiological compartments.

TABLE 3

| Mutations | SEQ ID NO | pH | DLS Percent PolyDispersity |
|---|---|---|---|
| None (wild-type) (200 μM) (6.3 mg/ml) | 2 | 5 | 23.35 |
|  |  | 6 | 19.3 |
|  |  | 7 | 21.65 |
|  |  | 8 | 30.15 |
|  |  | 9 | 21.9 |
| M61V, E75Q, M78K (200 μM) (6.9 mg/ml) | 3 | 5 | 16.35 |
|  |  | 6 | 21.2 |
|  |  | 7 | 17.6 |
|  |  | 8 | 29.55 |
|  |  | 9 | 16.8 |
| M61V, E75Q, M78K, S106R (200 μM) (6.4 mg/ml) | 5 | 5 | 9.85 |
|  |  | 6 | 19.4 |
|  |  | 7 | 22.1 |
|  |  | 8 | 21.25 |
|  |  | 9 | 25.2 |
| M61V, E75Q, M78K, I116F, E119Q (193 μM) (6.7 mg/ml) | 7 | 5 | 17 |
|  |  | 6 | 29.9 |
|  |  | 7 | 24.55 |
|  |  | 8 | 25.5 |
|  |  | 9 | 13.7 |

Example 3

This example demonstrates the ability of griffithsin mutants to neutralize HIV pseudovirus.

The anti-viral potency (IC50) of wild-type griffithsin and griffithsin mutants against HIV pseudoviruses (Q769.h5 and SF162) was determined using standard methods. As shown in Table 4, the griffithsin mutants have similar or more potent (IC50) ability than griffithsin to neutralize HIV pseudovirus.

TABLE 4

| Mutations | SEQ ID NO | IC50 (μg/mL) Q769.h5 | IC50 (μg/mL) SF162 |
|---|---|---|---|
| None (wild-type) | 2 | 0.09831 | 0.00008167 |
| M78A | 15 | 0.09084 | 0.00006044 |
| M78K | 16 | 0.04259 | 0.00004967 |
| M78L | 17 | 0.04784 | 0.00005891 |
| M78Q | 18 | 0.05847 | 0.00006237 |

Example 4

This example demonstrates the reduced oxidation observed for modified griffithsin polypeptides containing an M78Q substitution relative to the wild-type griffithsin sequence (SEQ ID NO: 2).

The polypeptide of SEQ ID NO: 18 (Q-GRFT) and wild-type griffithsin of SEQ ID NO: 2 were exposed to 0.02% hydrogen peroxide (biologically relevant level of hydrogen peroxide found in the human vagina) for 24 hours. The parent HPLC peaks of wild-type griffithsin and Q-GRFT were 0.16% and 86.24%, respectively. Additionally, intact mass spectrometry confirmed the increased stability of Q-GRFT over wild-type griffithsin after hydrogen peroxide (0.02% and 1.5%) exposure.

By minimizing the oxidative degradation, Q-GRFT will be more stable within a pharmaceutical dosage form and upon delivery within the human body. Additionally, a pharmaceutical dosage form comprising Q-GRFT will have a longer shelf-life and less instability issues than wild-type griffithsin.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and "at least one" and similar referents in the context of describing the invention (especially in the context of the following claims) are to be construed to cover both the singular and the plural, unless otherwise indicated herein or clearly contradicted by context. The use of the term "at least one" followed by a list of one or more items (for example, "at least one of A and B") is to be construed to mean one item selected from the listed items (A or B) or any combination of two or more of the listed items (A and B), unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The invention claimed is:

1. A polypeptide comprising the amino acid sequence of SLTHRKFGGSGGSPFSGLSSIAVRSGSYLDAIIIDGVH-HGGSGGNLSPTFTFGSGEYISN X$_1$TIRSGDYIDNISFX$_2$TNX$_3$GRRFGPYGGSGGS-ANTLSNVKVIQINGX$_4$X$_5$GDYLDSLD X$_6$YYX$_7$QY (SEQ ID NO: 1), wherein X$_1$ can be M or V, X$_2$ is Q, X$_3$ can be M, A, K, V, F, L, I, Q, R, or G, X$_4$ can be S or R, X$_5$ can be A or S, X$_6$ can be I or F, and X$_7$ can be E or Q provided that the polypeptide does not comprise the amino acid sequence of SEQ ID NO: 2.

2. The polypeptide of claim 1, wherein X$_3$ is Q.

3. The polypeptide of claim 1, wherein the polypeptide forms a dimer.

4. A conjugate comprising the polypeptide of claim 1, and at least one effector component.

5. The conjugate of claim 4, wherein the at least one effector component, which can be same or different, is selected from the group consisting of polyethylene glycol, albumin, dextran, a toxin, an immunological reagent, a virus, a viral envelope glycoprotein, an antiviral agent, and a solid support matrix.

6. A nucleic acid molecule encoding the polypeptide of claim 1.

7. The nucleic acid molecule of claim 6, wherein the nucleic acid molecule comprises the nucleotide sequence of SEQ ID NO: 4, 6, 8, or 10.

8. A vector comprising the nucleic acid molecule of claim 6.

9. A cell comprising the nucleic acid molecule of claim 6.

10. A composition comprising the polypeptide of claim 1, and a carrier.

11. A method of prophylactically or therapeutically inhibiting an viral infection in a cell or host comprising administering to the cell or host the polypeptide of claim 1, such that the viral infection is inhibited.

12. The method of claim 11, wherein the viral infection is an HIV infection.

13. A method of inhibiting a virus in a biological sample or in/on an inanimate object comprising contacting the biological sample or the inanimate object with a viral-inhibiting amount of the polypeptide of claim 1, which method optionally further comprises the prior, simultaneous, or subsequent contacting of the biological sample or inanimate object with an antiviral agent or another agent that is efficacious in inhibiting the virus, whereupon the virus is inhibited.

14. The polypeptide of claim 1, wherein $X_3$ is A, K, L, or Q.

15. The polypeptide of claim 1, wherein the polypeptide is a mutant griffithsin polypeptide.

16. A polypeptide consisting of the amino acid sequence of SEQ ID NO: 1.

* * * * *

UNITED STATES PATENT AND TRADEMARK OFFICE
CERTIFICATE OF CORRECTION

PATENT NO. : 10,501,507 B2
APPLICATION NO. : 15/550323
DATED : December 10, 2019
INVENTOR(S) : Barry R. O'Keefe et al.

It is certified that error appears in the above-identified patent and that said Letters Patent is hereby corrected as shown below:

In the Specification

Please insert the following Government Rights statement immediately after the priority claim in Column 1 Line 11 (approx.):

--Government Rights
This invention was made with government support under AI113182 and AI086177 awarded by the National Institutes of Health. The government has certain rights in the invention.--

Signed and Sealed this
Twenty-sixth Day of May, 2020

Andrei Iancu
*Director of the United States Patent and Trademark Office*

SEQUENCE LISTING

```
<160> NUMBER OF SEQ ID NOS: 18

<210> SEQ ID NO 1
<211> LENGTH: 121
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (61)..(61)
<223> OTHER INFORMATION: wherein X can be M or V
<220> FEATURE:
<221> NAME/KEY: MISC_FEATURE
<222> LOCATION: (75)..(75)
<223> OTHER INFORMATION: X can be E or Q
<220> FEATURE:
<221> NAME/KEY: MISC_FEATURE
<222> LOCATION: (78)..(78)
<223> OTHER INFORMATION: X can be M, A, K, V, F, L, I, Q, R, or G
<220> FEATURE:
<221> NAME/KEY: MISC_FEATURE
<222> LOCATION: (106)..(106)
<223> OTHER INFORMATION: X can be S or R
<220> FEATURE:
<221> NAME/KEY: MISC_FEATURE
```

```
<222> LOCATION: (107)..(107)
<223> OTHER INFORMATION: X can be A or S
<220> FEATURE:
<221> NAME/KEY: MISC_FEATURE
<222> LOCATION: (116)..(116)
<223> OTHER INFORMATION: X can be I or F
<220> FEATURE:
<221> NAME/KEY: MISC_FEATURE
<222> LOCATION: (119)..(119)
<223> OTHER INFORMATION: X can be E or Q

<400> SEQUENCE: 1

Ser Leu Thr His Arg Lys Phe Gly Gly Ser Gly Gly Ser Pro Phe Ser
1               5                   10                  15

Gly Leu Ser Ser Ile Ala Val Arg Ser Gly Ser Tyr Leu Asp Ala Ile
            20                  25                  30

Ile Ile Asp Gly Val His His Gly Gly Ser Gly Asn Leu Ser Pro
        35                  40                  45

Thr Phe Thr Phe Gly Ser Gly Glu Tyr Ile Ser Asn Xaa Thr Ile Arg
    50                  55                  60

Ser Gly Asp Tyr Ile Asp Asn Ile Ser Phe Xaa Thr Asn Xaa Gly Arg
65                  70                  75                  80

Arg Phe Gly Pro Tyr Gly Gly Ser Gly Gly Ser Ala Asn Thr Leu Ser
                85                  90                  95

Asn Val Lys Val Ile Gln Ile Asn Gly Xaa Xaa Gly Asp Tyr Leu Asp
            100                 105                 110

Ser Leu Asp Xaa Tyr Tyr Xaa Gln Tyr
        115                 120

<210> SEQ ID NO 2
<211> LENGTH: 121
<212> TYPE: PRT
<213> ORGANISM: Artificial Sequence
<220> FEATURE:
<223> OTHER INFORMATION: Synthetic

<400> SEQUENCE: 2

Ser Leu Thr His Arg Lys Phe Gly Gly Ser Gly Gly Ser Pro Phe Ser
1               5                   10                  15

Gly Leu Ser Ser Ile Ala Val Arg Ser Gly Ser Tyr Leu Asp Ala Ile
            20                  25                  30

Ile Ile Asp Gly Val His His Gly Gly Ser Gly Asn Leu Ser Pro
        35                  40                  45

Thr Phe Thr Phe Gly Ser Gly Glu Tyr Ile Ser Asn Met Thr Ile Arg
    50                  55                  60

Ser Gly Asp Tyr Ile Asp Asn Ile Ser Phe Glu Thr Asn Met Gly Arg
65                  70                  75                  80

Arg Phe Gly Pro Tyr Gly Gly Ser Gly Gly Ser Ala Asn Thr Leu Ser
                85                  90                  95

Asn Val Lys Val Ile Gln Ile Asn Gly Ser Ala Gly Asp Tyr Leu Asp
            100                 105                 110

Ser Leu Asp Ile Tyr Tyr Glu Gln Tyr
        115                 120

<210> SEQ ID NO 3
<211> LENGTH: 121
<212> TYPE: PRT
<213> ORGANISM: Artificial Sequence
<220> FEATURE:
<223> OTHER INFORMATION: Synthetic
```

<400> SEQUENCE: 3

```
Ser Leu Thr His Arg Lys Phe Gly Gly Ser Gly Gly Ser Pro Phe Ser
1               5                   10                  15

Gly Leu Ser Ser Ile Ala Val Arg Ser Gly Ser Tyr Leu Asp Ala Ile
            20                  25                  30

Ile Ile Asp Gly Val His His Gly Ser Gly Gly Asn Leu Ser Pro
        35                  40                  45

Thr Phe Thr Phe Gly Ser Gly Glu Tyr Ile Ser Asn Val Thr Ile Arg
    50                  55                  60

Ser Gly Asp Tyr Ile Asp Asn Ile Ser Phe Gln Thr Asn Lys Gly Arg
65                  70                  75                  80

Arg Phe Gly Pro Tyr Gly Gly Ser Gly Ser Ala Asn Thr Leu Ser
                85                  90                  95

Asn Val Lys Val Ile Gln Ile Asn Gly Ser Ala Gly Asp Tyr Leu Asp
            100                 105                 110

Ser Leu Asp Ile Tyr Tyr Glu Gln Tyr
            115                 120
```

<210> SEQ ID NO 4
<211> LENGTH: 366
<212> TYPE: DNA
<213> ORGANISM: Artificial Sequence
<220> FEATURE:
<223> OTHER INFORMATION: Synthetic

<400> SEQUENCE: 4

```
agcctgaccc atcgcaagtt cggtggtagt ggtggaagtc cgttctctgg tctgagcagc      60
attgcagttc gtagtggcag ctatctggat gcgatcatca ttgatggtgt acatcacggt     120
ggctctggtg gtaacctgag tccgaccttc acctttggat ccggtgagta catcagcaac     180
gtgaccattc gtagtggaga ctacattgac aacatcagct ttcaaaccaa caagggtcgt     240
cgctttggtc cgtatggtgg atctggtggc agtgcaaaca ccctgagcaa cgtgaaagtc     300
atccagatca acggtagtgc aggtgactat ctggatagcc tggacatcta ctatgaacag     360
tactaa                                                                366
```

<210> SEQ ID NO 5
<211> LENGTH: 121
<212> TYPE: PRT
<213> ORGANISM: Artificial Sequence
<220> FEATURE:
<223> OTHER INFORMATION: Synthetic

<400> SEQUENCE: 5

```
Ser Leu Thr His Arg Lys Phe Gly Gly Ser Gly Gly Ser Pro Phe Ser
1               5                   10                  15

Gly Leu Ser Ser Ile Ala Val Arg Ser Gly Ser Tyr Leu Asp Ala Ile
            20                  25                  30

Ile Ile Asp Gly Val His His Gly Gly Ser Gly Gly Asn Leu Ser Pro
        35                  40                  45

Thr Phe Thr Phe Gly Ser Gly Glu Tyr Ile Ser Asn Val Thr Ile Arg
    50                  55                  60

Ser Gly Asp Tyr Ile Asp Asn Ile Ser Phe Gln Thr Asn Lys Gly Arg
65                  70                  75                  80

Arg Phe Gly Pro Tyr Gly Gly Ser Gly Gly Ser Ala Asn Thr Leu Ser
                85                  90                  95

Asn Val Lys Val Ile Gln Ile Asn Gly Arg Ala Gly Asp Tyr Leu Asp
```

Ser Leu Asp Ile Tyr Tyr Glu Gln Tyr
    115             120

<210> SEQ ID NO 6
<211> LENGTH: 366
<212> TYPE: DNA
<213> ORGANISM: Artificial Sequence
<220> FEATURE:
<223> OTHER INFORMATION: Synthetic

<400> SEQUENCE: 6

```
agcctgaccc atcgcaagtt cggtggtagt ggtggaagtc cgttctctgg tctgagcagc      60
attgcagttc gtagtggcag ctatctggat gcgatcatca ttgatggtgt acatcacggt     120
ggctctggtg gtaacctgag tccgaccttc acctttggat ccggtgagta catcagcaac     180
gtgaccattc gtagtggaga ctacattgac aacatcagct ttcaaaccaa caagggtcgt     240
cgctttggtc cgtatggtgg atctggtggc agtgcaaaca ccctgagcaa cgtgaaagtc     300
atccagatca acggtcgtgc aggtgactat ctggatagcc tggacatcta ctatgaacag     360
tactaa                                                                366
```

<210> SEQ ID NO 7
<211> LENGTH: 121
<212> TYPE: PRT
<213> ORGANISM: Artificial Sequence
<220> FEATURE:
<223> OTHER INFORMATION: Synthetic

<400> SEQUENCE: 7

Ser Leu Thr His Arg Lys Phe Gly Gly Ser Gly Gly Ser Pro Phe Ser
1               5                   10                  15

Gly Leu Ser Ser Ile Ala Val Arg Ser Gly Ser Tyr Leu Asp Ala Ile
            20                  25                  30

Ile Ile Asp Gly Val His His Gly Gly Ser Gly Gly Asn Leu Ser Pro
        35                  40                  45

Thr Phe Thr Phe Gly Ser Gly Glu Tyr Ile Ser Asn Val Thr Ile Arg
    50                  55                  60

Ser Gly Asp Tyr Ile Asp Asn Ile Ser Phe Gln Thr Asn Lys Gly Arg
65                  70                  75                  80

Arg Phe Gly Pro Tyr Gly Gly Ser Gly Gly Ser Ala Asn Thr Leu Ser
                85                  90                  95

Asn Val Lys Val Ile Gln Ile Asn Gly Ser Ala Gly Asp Tyr Leu Asp
            100                 105                 110

Ser Leu Asp Phe Tyr Tyr Gln Gln Tyr
    115             120

<210> SEQ ID NO 8
<211> LENGTH: 366
<212> TYPE: DNA
<213> ORGANISM: Artificial Sequence
<220> FEATURE:
<223> OTHER INFORMATION: Synthetic

<400> SEQUENCE: 8

```
agcctgaccc atcgcaagtt cggtggtagt ggtggaagtc cgttctctgg tctgagcagc      60
attgcagttc gtagtggcag ctatctggat gcgatcatca ttgatggtgt acatcacggt     120
ggctctggtg gtaacctgag tccgaccttc acctttggat ccggtgagta catcagcaac     180
```

```
gtgaccattc gtagtggaga ctacattgac aacatcagct ttcaaaccaa caagggtcgt      240
cgctttggtc cgtatggtgg atctggtggc agtgcaaaca ccctgagcaa cgtgaaagtc      300
atccagatca acggtagtgc aggtgactat ctggatagcc tggacttcta ctatcagcag      360
tactaa                                                                 366
```

```
<210> SEQ ID NO 9
<211> LENGTH: 121
<212> TYPE: PRT
<213> ORGANISM: Artificial Sequence
<220> FEATURE:
<223> OTHER INFORMATION: Synthetic

<400> SEQUENCE: 9

Ser Leu Thr His Arg Lys Phe Gly Gly Ser Gly Gly Ser Pro Phe Ser
1               5                   10                  15

Gly Leu Ser Ser Ile Ala Val Arg Ser Gly Ser Tyr Leu Asp Ala Ile
            20                  25                  30

Ile Ile Asp Gly Val His His Gly Gly Ser Gly Gly Asn Leu Ser Pro
        35                  40                  45

Thr Phe Thr Phe Gly Ser Gly Glu Tyr Ile Ser Asn Met Thr Ile Arg
    50                  55                  60

Ser Gly Asp Tyr Ile Asp Asn Ile Ser Phe Gln Thr Asn Lys Gly Arg
65                  70                  75                  80

Arg Phe Gly Pro Tyr Gly Gly Ser Gly Gly Ser Ala Asn Thr Leu Ser
                85                  90                  95

Asn Val Lys Val Ile Gln Ile Asn Gly Arg Ala Gly Asp Tyr Leu Asp
            100                 105                 110

Ser Leu Asp Ile Tyr Tyr Glu Gln Tyr
        115                 120
```

```
<210> SEQ ID NO 10
<211> LENGTH: 366
<212> TYPE: DNA
<213> ORGANISM: Artificial Sequence
<220> FEATURE:
<223> OTHER INFORMATION: Synthetic

<400> SEQUENCE: 10
agcctgaccc atcgcaagtt cggtggtagt ggtggaagtc cgttctctgg tctgagcagc      60
attgcagttc gtagtggcag ctatctggat gcgatcatca ttgatggtgt acatcacggt     120
ggctctggtg gtaacctgag tccgaccttc acctttggat ccggtgagta catcagcaac     180
atgaccattc gtagtggaga ctacattgac aacatcagct ttcaaaccaa caagggtcgt     240
cgctttggtc cgtatggtgg atctggtggc agtgcaaaca ccctgagcaa cgtgaaagtc     300
atccagatca acggtcgtgc aggtgactat ctggatagcc tggacatcta ctatgaacag     360
tactaa                                                                366
```

```
<210> SEQ ID NO 11
<211> LENGTH: 121
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (61)..(61)
<223> OTHER INFORMATION: wherein X is M
<220> FEATURE:
<221> NAME/KEY: MISC_FEATURE
```

<222> LOCATION: (75)..(75)
<223> OTHER INFORMATION: wherein X is Q
<220> FEATURE:
<221> NAME/KEY: MISC_FEATURE
<222> LOCATION: (78)..(78)
<223> OTHER INFORMATION: wherein X is K, V, or A
<220> FEATURE:
<221> NAME/KEY: MISC_FEATURE
<222> LOCATION: (106)..(106)
<223> OTHER INFORMATION: wherein X is S
<220> FEATURE:
<221> NAME/KEY: MISC_FEATURE
<222> LOCATION: (107)..(107)
<223> OTHER INFORMATION: wherein X is A
<220> FEATURE:
<221> NAME/KEY: MISC_FEATURE
<222> LOCATION: (116)..(116)
<223> OTHER INFORMATION: wherein X is I
<220> FEATURE:
<221> NAME/KEY: MISC_FEATURE
<222> LOCATION: (119)..(119)
<223> OTHER INFORMATION: wherein X is E

<400> SEQUENCE: 11

Ser Leu Thr His Arg Lys Phe Gly Gly Ser Gly Gly Ser Pro Phe Ser
1               5                   10                  15

Gly Leu Ser Ser Ile Ala Val Arg Ser Gly Ser Tyr Leu Asp Ala Ile
            20                  25                  30

Ile Ile Asp Gly Val His His Gly Ser Gly Gly Asn Leu Ser Pro
        35                  40                  45

Thr Phe Thr Phe Gly Ser Gly Glu Tyr Ile Ser Asn Xaa Thr Ile Arg
    50                  55                  60

Ser Gly Asp Tyr Ile Asp Asn Ile Ser Phe Xaa Thr Asn Xaa Gly Arg
65                  70                  75                  80

Arg Phe Gly Pro Tyr Gly Gly Ser Gly Gly Ser Ala Asn Thr Leu Ser
                85                  90                  95

Asn Val Lys Val Ile Gln Ile Asn Gly Xaa Xaa Gly Asp Tyr Leu Asp
            100                 105                 110

Ser Leu Asp Xaa Tyr Tyr Xaa Gln Tyr
        115                 120

<210> SEQ ID NO 12
<211> LENGTH: 121
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (61)..(61)
<223> OTHER INFORMATION: wherein X is M
<220> FEATURE:
<221> NAME/KEY: MISC_FEATURE
<222> LOCATION: (75)..(75)
<223> OTHER INFORMATION: wherein X is Q
<220> FEATURE:
<221> NAME/KEY: MISC_FEATURE
<222> LOCATION: (78)..(78)
<223> OTHER INFORMATION: wherein X is K
<220> FEATURE:
<221> NAME/KEY: MISC_FEATURE
<222> LOCATION: (106)..(106)
<223> OTHER INFORMATION: wherein X is S
<220> FEATURE:
<221> NAME/KEY: MISC_FEATURE
<222> LOCATION: (107)..(107)
<223> OTHER INFORMATION: wherein X is A
<220> FEATURE:
<221> NAME/KEY: MISC_FEATURE
<222> LOCATION: (116)..(116)

```
<223> OTHER INFORMATION: wherein X is I
<220> FEATURE:
<221> NAME/KEY: MISC_FEATURE
<222> LOCATION: (119)..(119)
<223> OTHER INFORMATION: wherein X is Q

<400> SEQUENCE: 12

Ser Leu Thr His Arg Lys Phe Gly Gly Ser Gly Gly Ser Pro Phe Ser
1               5                   10                  15

Gly Leu Ser Ser Ile Ala Val Arg Ser Gly Ser Tyr Leu Asp Ala Ile
            20                  25                  30

Ile Ile Asp Gly Val His His Gly Gly Ser Gly Gly Asn Leu Ser Pro
        35                  40                  45

Thr Phe Thr Phe Gly Ser Gly Glu Tyr Ile Ser Asn Xaa Thr Ile Arg
    50                  55                  60

Ser Gly Asp Tyr Ile Asp Asn Ile Ser Phe Xaa Thr Asn Xaa Gly Arg
65                  70                  75                  80

Arg Phe Gly Pro Tyr Gly Gly Ser Gly Gly Ser Ala Asn Thr Leu Ser
                85                  90                  95

Asn Val Lys Val Ile Gln Ile Asn Gly Xaa Xaa Gly Asp Tyr Leu Asp
            100                 105                 110

Ser Leu Asp Xaa Tyr Tyr Xaa Gln Tyr
            115                 120

<210> SEQ ID NO 13
<211> LENGTH: 121
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (61)..(61)
<223> OTHER INFORMATION: wherein X is V
<220> FEATURE:
<221> NAME/KEY: MISC_FEATURE
<222> LOCATION: (75)..(75)
<223> OTHER INFORMATION: wherein X is Q
<220> FEATURE:
<221> NAME/KEY: MISC_FEATURE
<222> LOCATION: (78)..(78)
<223> OTHER INFORMATION: wherein X is K
<220> FEATURE:
<221> NAME/KEY: MISC_FEATURE
<222> LOCATION: (106)..(106)
<223> OTHER INFORMATION: wherein X is S
<220> FEATURE:
<221> NAME/KEY: MISC_FEATURE
<222> LOCATION: (107)..(107)
<223> OTHER INFORMATION: wherein X is A
<220> FEATURE:
<221> NAME/KEY: MISC_FEATURE
<222> LOCATION: (116)..(116)
<223> OTHER INFORMATION: wherein X is I
<220> FEATURE:
<221> NAME/KEY: MISC_FEATURE
<222> LOCATION: (119)..(119)
<223> OTHER INFORMATION: wherein X is Q

<400> SEQUENCE: 13

Ser Leu Thr His Arg Lys Phe Gly Gly Ser Gly Gly Ser Pro Phe Ser
1               5                   10                  15

Gly Leu Ser Ser Ile Ala Val Arg Ser Gly Ser Tyr Leu Asp Ala Ile
            20                  25                  30

Ile Ile Asp Gly Val His His Gly Gly Ser Gly Gly Asn Leu Ser Pro
        35                  40                  45
```

```
Thr Phe Thr Phe Gly Ser Gly Glu Tyr Ile Ser Asn Xaa Thr Ile Arg
    50                  55                  60

Ser Gly Asp Tyr Ile Asp Asn Ile Ser Phe Xaa Thr Asn Xaa Gly Arg
 65              70                  75                  80

Arg Phe Gly Pro Tyr Gly Gly Ser Gly Gly Ser Ala Asn Thr Leu Ser
                 85                  90                  95

Asn Val Lys Val Ile Gln Ile Asn Gly Xaa Xaa Gly Asp Tyr Leu Asp
            100                 105                 110

Ser Leu Asp Xaa Tyr Tyr Xaa Gln Tyr
            115                 120
```

<210> SEQ ID NO 14
<211> LENGTH: 121
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (61)..(61)
<223> OTHER INFORMATION: wherein X is M
<220> FEATURE:
<221> NAME/KEY: MISC_FEATURE
<222> LOCATION: (75)..(75)
<223> OTHER INFORMATION: wherein X is Q
<220> FEATURE:
<221> NAME/KEY: MISC_FEATURE
<222> LOCATION: (78)..(78)
<223> OTHER INFORMATION: wherein X is K
<220> FEATURE:
<221> NAME/KEY: MISC_FEATURE
<222> LOCATION: (106)..(106)
<223> OTHER INFORMATION: wherein X is S
<220> FEATURE:
<221> NAME/KEY: MISC_FEATURE
<222> LOCATION: (107)..(107)
<223> OTHER INFORMATION: wherein X is A
<220> FEATURE:
<221> NAME/KEY: MISC_FEATURE
<222> LOCATION: (116)..(116)
<223> OTHER INFORMATION: wherein X is F
<220> FEATURE:
<221> NAME/KEY: MISC_FEATURE
<222> LOCATION: (119)..(119)
<223> OTHER INFORMATION: wherein X is Q

<400> SEQUENCE: 14

```
Ser Leu Thr His Arg Lys Phe Gly Gly Ser Gly Gly Ser Pro Phe Ser
 1               5                  10                  15

Gly Leu Ser Ser Ile Ala Val Arg Ser Gly Ser Tyr Leu Asp Ala Ile
             20                  25                  30

Ile Ile Asp Gly Val His His Gly Gly Ser Gly Gly Asn Leu Ser Pro
            35                  40                  45

Thr Phe Thr Phe Gly Ser Gly Glu Tyr Ile Ser Asn Xaa Thr Ile Arg
    50                  55                  60

Ser Gly Asp Tyr Ile Asp Asn Ile Ser Phe Xaa Thr Asn Xaa Gly Arg
 65              70                  75                  80

Arg Phe Gly Pro Tyr Gly Gly Ser Gly Gly Ser Ala Asn Thr Leu Ser
                 85                  90                  95

Asn Val Lys Val Ile Gln Ile Asn Gly Xaa Xaa Gly Asp Tyr Leu Asp
            100                 105                 110

Ser Leu Asp Xaa Tyr Tyr Xaa Gln Tyr
            115                 120
```

<210> SEQ ID NO 15

```
<211> LENGTH: 121
<212> TYPE: PRT
<213> ORGANISM: Artificial Sequence
<220> FEATURE:
<223> OTHER INFORMATION: Synthetic

<400> SEQUENCE: 15

Ser Leu Thr His Arg Lys Phe Gly Gly Ser Gly Gly Ser Pro Phe Ser
1               5                   10                  15

Gly Leu Ser Ser Ile Ala Val Arg Ser Gly Ser Tyr Leu Asp Ala Ile
            20                  25                  30

Ile Ile Asp Gly Val His His Gly Gly Ser Gly Gly Asn Leu Ser Pro
        35                  40                  45

Thr Phe Thr Phe Gly Ser Gly Glu Tyr Ile Ser Asn Met Thr Ile Arg
    50                  55                  60

Ser Gly Asp Tyr Ile Asp Asn Ile Ser Phe Glu Thr Asn Ala Gly Arg
65                  70                  75                  80

Arg Phe Gly Pro Tyr Gly Gly Ser Gly Gly Ser Ala Asn Thr Leu Ser
                85                  90                  95

Asn Val Lys Val Ile Gln Ile Asn Gly Ser Ala Gly Asp Tyr Leu Asp
            100                 105                 110

Ser Leu Asp Ile Tyr Tyr Glu Gln Tyr
        115                 120

<210> SEQ ID NO 16
<211> LENGTH: 121
<212> TYPE: PRT
<213> ORGANISM: Artificial Sequence
<220> FEATURE:
<223> OTHER INFORMATION: Synthetic

<400> SEQUENCE: 16

Ser Leu Thr His Arg Lys Phe Gly Gly Ser Gly Gly Ser Pro Phe Ser
1               5                   10                  15

Gly Leu Ser Ser Ile Ala Val Arg Ser Gly Ser Tyr Leu Asp Ala Ile
            20                  25                  30

Ile Ile Asp Gly Val His His Gly Gly Ser Gly Gly Asn Leu Ser Pro
        35                  40                  45

Thr Phe Thr Phe Gly Ser Gly Glu Tyr Ile Ser Asn Met Thr Ile Arg
    50                  55                  60

Ser Gly Asp Tyr Ile Asp Asn Ile Ser Phe Glu Thr Asn Lys Gly Arg
65                  70                  75                  80

Arg Phe Gly Pro Tyr Gly Gly Ser Gly Gly Ser Ala Asn Thr Leu Ser
                85                  90                  95

Asn Val Lys Val Ile Gln Ile Asn Gly Ser Ala Gly Asp Tyr Leu Asp
            100                 105                 110

Ser Leu Asp Ile Tyr Tyr Glu Gln Tyr
        115                 120

<210> SEQ ID NO 17
<211> LENGTH: 121
<212> TYPE: PRT
<213> ORGANISM: Artificial Sequence
<220> FEATURE:
<223> OTHER INFORMATION: Synthetic

<400> SEQUENCE: 17

Ser Leu Thr His Arg Lys Phe Gly Gly Ser Gly Gly Ser Pro Phe Ser
1               5                   10                  15
```

```
Gly Leu Ser Ser Ile Ala Val Arg Ser Gly Ser Tyr Leu Asp Ala Ile
            20                  25                  30

Ile Ile Asp Gly Val His His Gly Gly Ser Gly Gly Asn Leu Ser Pro
            35                  40                  45

Thr Phe Thr Phe Gly Ser Gly Glu Tyr Ile Ser Asn Met Thr Ile Arg
            50                  55                  60

Ser Gly Asp Tyr Ile Asp Asn Ile Ser Phe Glu Thr Asn Leu Gly Arg
65                  70                  75                  80

Arg Phe Gly Pro Tyr Gly Gly Ser Gly Gly Ser Ala Asn Thr Leu Ser
                85                  90                  95

Asn Val Lys Val Ile Gln Ile Asn Gly Ser Ala Gly Asp Tyr Leu Asp
            100                 105                 110

Ser Leu Asp Ile Tyr Tyr Glu Gln Tyr
            115                 120

<210> SEQ ID NO 18
<211> LENGTH: 121
<212> TYPE: PRT
<213> ORGANISM: Artificial Sequence
<220> FEATURE:
<223> OTHER INFORMATION: Synthetic

<400> SEQUENCE: 18

Ser Leu Thr His Arg Lys Phe Gly Gly Ser Gly Gly Ser Pro Phe Ser
1               5                   10                  15

Gly Leu Ser Ser Ile Ala Val Arg Ser Gly Ser Tyr Leu Asp Ala Ile
            20                  25                  30

Ile Ile Asp Gly Val His His Gly Gly Ser Gly Gly Asn Leu Ser Pro
            35                  40                  45

Thr Phe Thr Phe Gly Ser Gly Glu Tyr Ile Ser Asn Met Thr Ile Arg
            50                  55                  60

Ser Gly Asp Tyr Ile Asp Asn Ile Ser Phe Glu Thr Asn Gln Gly Arg
65                  70                  75                  80

Arg Phe Gly Pro Tyr Gly Gly Ser Gly Gly Ser Ala Asn Thr Leu Ser
                85                  90                  95

Asn Val Lys Val Ile Gln Ile Asn Gly Ser Ala Gly Asp Tyr Leu Asp
            100                 105                 110

Ser Leu Asp Ile Tyr Tyr Glu Gln Tyr
            115                 120
```